United States Patent [19]

Sanchez et al.

[11] Patent Number: 5,380,711
[45] Date of Patent: Jan. 10, 1995

[54] METHODS FOR DELIPIDATION OF SKIN AND CERUMEN REMOVAL

[75] Inventors: Robert A. Sanchez, Carlsbad; Sheldon S. Hendler, La Jolla, both of Calif.

[73] Assignee: Vyrex Corporation, La Jolla, Calif.

[21] Appl. No.: 212,856

[22] Filed: Mar. 15, 1994

Related U.S. Application Data

[63] Continuation-in-part of Ser. No. 40,052, Mar. 30, 1993, Pat. No. 5,296,472, Continuation-in-part of Ser. No. 76,276, Jul. 2, 1993, each is a continuation-in-part of Ser. No. 805,724, Sep. 17, 1993, abandoned.

[51] Int. Cl.$^6$ .................. A61K 31/70; A61K 31/715
[52] U.S. Cl. .................................... 514/58; D24/115; D24/119; 514/956
[58] Field of Search .............. 514/58, 846, 859, 863, 514/881, 969, 864; 424/61, 69, 70; D24/115, 119

[56] References Cited

U.S. PATENT DOCUMENTS

| | | | |
|---|---|---|---|
| 2,680,441 | 6/1954 | Krammer | 215/11.1 |
| 3,651,808 | 3/1972 | White | 604/54 |
| 3,872,866 | 3/1975 | Lelicoff | 604/54 |
| 4,234,103 | 11/1980 | Strobl, Jr. et al. | 222/89 |
| 4,492,759 | 1/1985 | Gorman et al. | 436/72 |
| 4,566,613 | 1/1986 | Anscomb | 222/541 |
| 4,821,895 | 4/1989 | Roskilly | 215/11.1 |
| 4,995,867 | 2/1991 | Zollinger | 604/54 |
| 5,029,701 | 7/1991 | Roth et al. | 206/232 |

FOREIGN PATENT DOCUMENTS

| | | |
|---|---|---|
| 2640136 | 6/1990 | France . |
| 1-193209 | 8/1989 | Japan . |
| 3-287512 | 12/1991 | Japan . |

Primary Examiner—Ronald W. Griffin
Attorney, Agent, or Firm—Glenna Hendricks; Stephen Gates

[57] ABSTRACT

The present invention provides delipidating compositions containing essentially oil-free "empty" cyclodextrin compositions. It also provides compositions for use in removal of cerumen from the ear. The compositions containing "empty" cyclodextrin advantageously avoid use of harsh, drying agents or injurious mechanical methods.

4 Claims, No Drawings

METHODS FOR DELIPIDATION OF SKIN AND CERUMEN REMOVAL

This application is a continuation-in-part of U.S. Ser. No. 08/040,052 filed Mar. 30, 1993, now U.S. Pat. No. 5,296,472, and 08/076,276 filed Jul. 2, 1993, both pending, which are continuations-in-part of U.S. Ser. No. 07/805,724 filed Sep. 17, 1993, now abandoned.

FIELD OF THE INVENTION

This invention is related to methods of removing lipids from the skin and hair and for removing cerumen from the ear canal.

BACKGROUND OF THE INVENTION

Sebaceous glands secrete sebum which contain lipids which collect on the skin and in the ear canal. The rate of secretion depends on several factors. Several skin disorders, including acne and seborrhea, are associated with inappropriate sebum production.

The removal of excess lipids from the skin can usually be accomplished by bathing using detergents and cleansers. Many preparations have been developed to assist in removal of excess lipids. U.S. Pat. No. 5,026,551 discloses compositions comprising carbon dioxide gas and emulsifiers with oils in bath preparations. In one embodiment the carbon dioxide gas was carried on cyclodextrin. U.S. Pat. No. 4,970,072 discloses use of whey products in bath preparations.

Cyclodextrins have been used as delivery agents for water-insoluble drugs for topical, oral and parenteral delivery. They have also been used to deliver cosmetic preparations to the skin. Several compositions utilize cyclodextrin inclusion products. European patent application 0 366 154 (1990) discloses several cyclodextrin inclusion products for use in cosmetic compositions. U.S. Pat. No. 4,678,598 discloses and claims a cyclodextrin-containing shampoo containing menthol and camphor. The cyclodextrin is provided to depress odor. U.S. Pat. No. 4,267,166 discloses use of cyclodextrin to treat foul breath. U.S. Pat. No. 4,891,361 discloses use of a kojic/cyclodextrin inclusion complexes to prevent elastosis in an animal test by preventing formation of melanin. A publication of Wacker Chemicals discloses that empty cyclodextrins in powder or creams may contain excreted matter of the skin or reaction substances produced on the skin. The statement by Wacker is under a subheading, "masking of disagreeable smells" and contains four other statements, all of which pertain to odorous substances. The sebaceous skin lipids are not odorous. Therefore, is appears that the Wacker publication was referring to the containment of unpleasant odors that are produced when bacteria act upon lipids and other skin secretions. There is no evidence therein the materials were useful as cleansing agents for delipidation of the skin.

SUMMARY OF THE INVENTION

The present invention provides delipidating compositions containing essentially oil-free "empty" cyclodextrin compositions. It also provides compositions for use in removal of cerumen from the ear. The compositions containing "empty" cyclodextrin advantageously avoid use of harsh, drying agents or injurious mechanical methods.

DETAILED DESCRIPTION OF THE INVENTION

Cyclodextrins are cyclic oligomers of glucose that are derived from starch, and that consist of rings of glucose molecules. The three most common forms, alpha-, beta-, and gamma-cyclodextrins consist, respectively, of six, seven and eight glucose molecules. The molecules contain cavities that have lipophilic properties. Cyclodextrins present an advantage as natural substances that are nontoxic and nonirritating to the skin. Empty cyclodextrins have often been sold for use in preparation of inclusion complexes. Formulations of the invention are essentially non-irritating and non-allergenic. Compositions for use in delipidation should be essentially free of oil. The compositions of the invention are basically dry solids or aqueous solutions containing empty (uncomplexed) or loosely complexed cyclodextrin. For example, $\alpha$-, $\beta$- and $\gamma$-cyclodextrins, including substituted cyclodextrins may be used. The $\beta$- and $\gamma$-cyclodextrins appear to be particularly useful in the methods of the invention. The hydroxypropyl cyclodextrins ere particularly useful either alone or in combination with other cyclodextrins. It is often useful to use more than one cyclodextrin so that there are different "holes" for purposes of complexing different substances in the ear canal or on the skin.

The use of cyclodextrins on a support provides a useful means of application and treatment of patients who have conditions such as seborrhea or acne. The cyclodextrin is adsorbed or absorbed on or in the support. Supports may be, for example, a gauze, a sponge, cellulose such a paper, or polymeric sheets and fabrics. The supports with the cyclodextrin may be placed in air-tight packaging such as foil or plastic sheets which are sealed. For emergency facilities they may be provided in containers of multiple pre-moistened supports. The cyclodextrin compositions may also be placed in containers with dispensing means such as roll-on means, brushes, sponges, or fabrics which may placed at the container opening or be attached to the cap for easy application to affected areas. The administration of cyclodextrins using moistened supports allows targeted delivery of the cyclodextrin-containing solution. Pre-moistened sheets provide a preferred method for continued exposure of the tissue to the cyclodextrin solution. Compositions for use in the method of the invention can also be applied as aerosols to be sprayed on the target area or sprayed on supports for application to the target area. Other methods of application include roll-on, application by hand or brush or other means. Another method of application is by immersion in or sprinkling by water containing the cyclodextrin. Suitable carriers may be in the form of powder, oil-free gels or suspensions. However, the carrier must not contain any component that complexes with the cyclodextrin in such a manner that it is not readily replaced by components to be removed from the skin or ear canal.

Aqueous compositions are a preferred class of compositions. However, the compositions may contain alcohols or other carriers that are not firmly complexed to the cyclodextrin. The primary requirement of any composition of the invention is that the cyclodextrin either be empty of guest molecules or, if some component of the composition can be complexed, the guest molecules must be preferentially and easily displaced by lipids or lipid-like materials.

Compositions for use in the ear canal may also be provided in the form of gels, lotions, and creams. However, it is crucial that the composition contain no complexed molecules that are not easily displaced by components of cerumen, which is a mixture of debris, hair, dirt, and various lipid-like substances which include fatty acids and waxes. The components differ among patients.

For use in the ear canal, cyclodextrins in aqueous carriers present advantages of economy and ease of use. Cyclodextrin solutions containing between 1 and 30% by weight are preferred. A preferred concentration is about 10%. For use on the skin, the compositions may be in the form of powders or of liquid formulations. It is important that no components of the composition bind to the cyclodextrin which might fill the cyclodextrin cavity or render the cavity unaccessible, i.e., no additive should interfere with the complexing of lipids by the cyclodextrins. Because cerumen is a heterogeneous mixture of lipid-like substances, mixtures of cyclodextrins having different cavity sizes may be advantageously used in compositions for cleansing of the ear canal.

Compositions may also be used to delipidate hair and the scalp. Such compositions may be in the form of aqueous solutions for use as rinses or shampoos.

EXAMPLE 1

Dissolution of Skin Lipids

Sebum and other skin lipids were collected from facial skin by gentle scraping with a spatula. Small amounts of the lipid were applied to glass slides as thin smears, approximately 50 $\mu$g/20 mm$^2$. One slide (a) was covered with a water layer and the other slide (b) was covered with a 5% solution of hydroxypropyl-$\beta$-cyclodextrin in water. The slides were shaken gently periodically at room temperature, and were then examined by transmitted light. No obvious changes were observed on the lipid smear of slide (a) over 30 minutes time. On slide (b), evidence of dissipation of lipids was seen in a few minutes. After 30 minutes, most of the lipid on slide (b) was gone, and the aqueous phase remained clear.

EXAMPLE 2

Dissolution of Cerumen

The procedure of Example 1 was followed using cerumen collected from the ear. The results were similar to those obtained with sebum.

EXAMPLE 3

Absorption of Lipids

Glass slides containing thin smears of skin lipids were prepared as in example 1. Slide (a) was an untreated control. Powdered $\beta$-cyclodextrin was placed over the lipid layer of slide (b) and gently pressed down with a flat spatula without triturating or mixing. After D minutes at room temperature, both sides were gently rinsed several times with distilled water. Both were covered with water and examined by transmitted light. Slide (a) appeared to be substantially unchanged, and the film strongly repelled water. Only a trace of film remained on slide (b), and water was not repelled from the area where the smear had been applied.

EXAMPLE 4

Skin Test

A female applied a very thin layer of $\beta$-cyclodextrin in water suspension to one side of the face and nose. The suspension applied smoothly and easily and gave a sensation of coolness. For a period of 4–6 hours thereafter, the treated skin appeared oil-free and lacked the shiny, moist, oily appearance of the untreated area.

EXAMPLE 5

Skin Test

A male applied a very thin layer of powdered beta-cyclodextrin to one side of the face and nose, using his finger as an applicator. The powder applied smoothly and easily. The white powder was no longer visible after several minutes. The subject male remained in a warm room for two hours. Areas wherein the cyclodextrin had been applied appeared oil-free. Untreated areas had a shiny appearance and a moist, oily texture.

The test was repeated with powdered hydroxypropyl-$\beta$-cyclodextrin. Similar results were obtained. The test using hydroxpropyl-$\beta$-cyclodextrin was repeated. However, water was sprayed on the face after several minutes. Water on the untreated side formed droplets, indicating presence of lipids on the skin. Droplet formation was far less on the side which had been treated with cyclodextrin.

EXAMPLE 6

Cerumen Complexation

Multiple samples of cerumen were prepared in the following manner: Ear wax from several patients was collected and combined with water by ultrasonication. The resulting suspension was coarsely filtered to remove hair and large particles. Aliquots of the suspension were then spotted onto polyethylene sheets and dried with warm air to form a yellowish waxy cerumen layer. The polyethylene sheets were cut into disks, each containing about 7 milligrams of cerumen.

Disks were placed in tubes containing different formulations:

1: 10% weight aqueous solution of $\gamma$-cyclodextrin.
2: Debrox from Marion Merrell Dow, Cincinnati, Ohio, containing urea, peroxide, glycols and water.
3: Cerumenex from Purdue Frederick, Norwalk, Conn., containing peptide oleate condensate and propylene glycol.

Results after 10 minutes:

1: cerumen began to separate from the plastic disk, color was lightened, and cerumen/dextran complex had accumulated at the bottom of the tube. Upon swirling, the cerumen completely separated from the polyethylene disk and disintegrated.
2 Small bubbles formed. Cerumen retained yellowish color and remained affixed to the polyethylene disks even after swirling.
3 No bubbles. Cerumen retained yellowish color and remained affixed to the polyethylene disks even after swirling.

EXAMPLE 7

Cerumen Removal in Human Patients

Compositions of Example 6 were tested in two human subjects. In each instance, the solution was warmed to body temperature and the ear canal filled with 20–30 drops of the solution. After 10 minutes, the solution was drained from the ear canal into a clear cup. The canal was then examined by otoscope.

In subject #I, Compositions #1 and #2 were tested by treating one ear with composition #1 and the other with composition #2. Results:

Patient #I

Composition #1: Substantial reduction in cerumen was noted. Recovered solution was cloudy and contained visible particles. No irritation was reported.

Composition #2: Little change in amount of cerumen in the ear. Solution recovered was substantially clear. No irritation was reported.

Patient #II

Composition #1: Result was same as in patient #I.

Compositions #3: Result essentially the same as in patient #I when treated with composition #2, except that some irritation was reported several hours later.

EXAMPLE 8

Cerumen Removal in an AIDS Patient

Solution #1 containing 10% $\gamma$-cyclodextrin in water was applied to ears by the method of Example 7. Ears were substantially cleared of wax. No irritation was reported.

The methods of the invention are particularly useful in immune compromised patients or patients with easily injured skin such as the elderly or children, since no mechanically abrasive method is required in practice of the invention.

The compositions for use in removing cerumen may advantageously be sold in bottles having tops equipped with droppers for administration into the ear canal. It is also possible to provide the droppers with the bottles or to provide kits for adminstration of the cyclodextrin-containing material for cleaning the ears using droppers and ear syringes for further cleaning of the ear.

Compositions for use in delipidation of the skin may be supplied on saturated sponges or other absorbent materials in sealed packages or may be provided in bottles with or without supports on which to adsorb the materials for application to the skin.

Delipidating compositions may contain, additionally, fragrances, colorants and other additives used in the cosmetic and hair-care art so long as such additives are not strongly complexed by the cyclodextrin.

We claim:

1. A bottle with a closure means containing substantially oil-free cyclodextrin-containing composition wherein said closure means has a dropper appropriate for instillation of said cyclodextrin into the ear attached thereto.

2. A bottle of claim 1 wherein the cyclodextrins are selected from the group consisting of $\alpha$-cyclodextrins, $\beta$-cyclodextrins and $\gamma$-cyclodextrins.

3. A bottle of claim 1 wherein containing cyclodextrins of at least two different cavity sizes.

4. A kit containing a substantially oil-free cyclodextrin-containing composition, said kit also containing a dropper appropriate for instillation of said cyclodextrin into the ear and an ear syringe.

* * * * *